United States Patent [19]

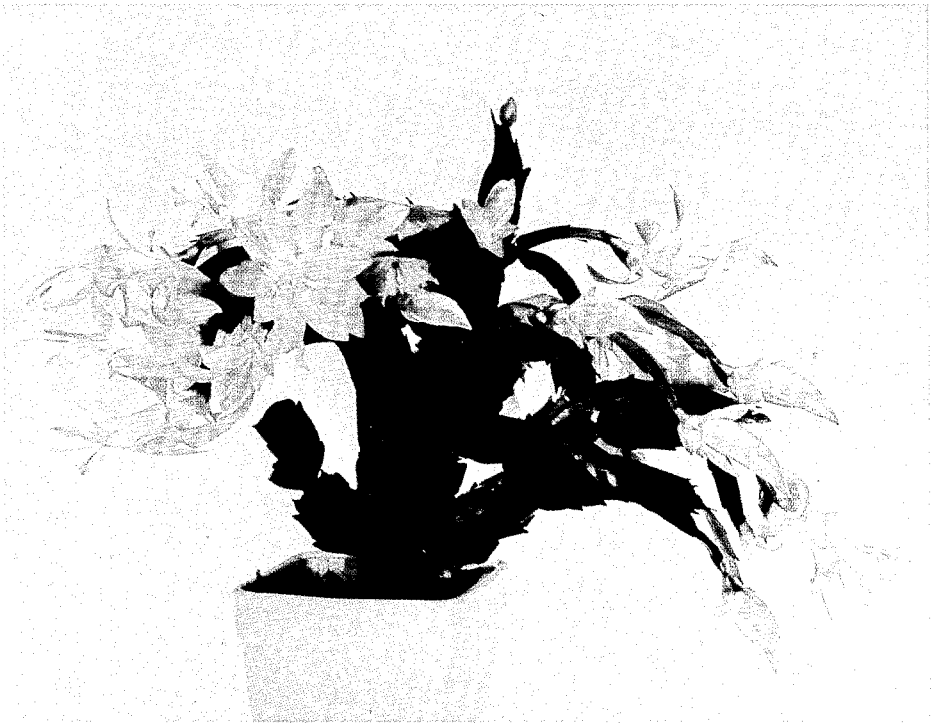
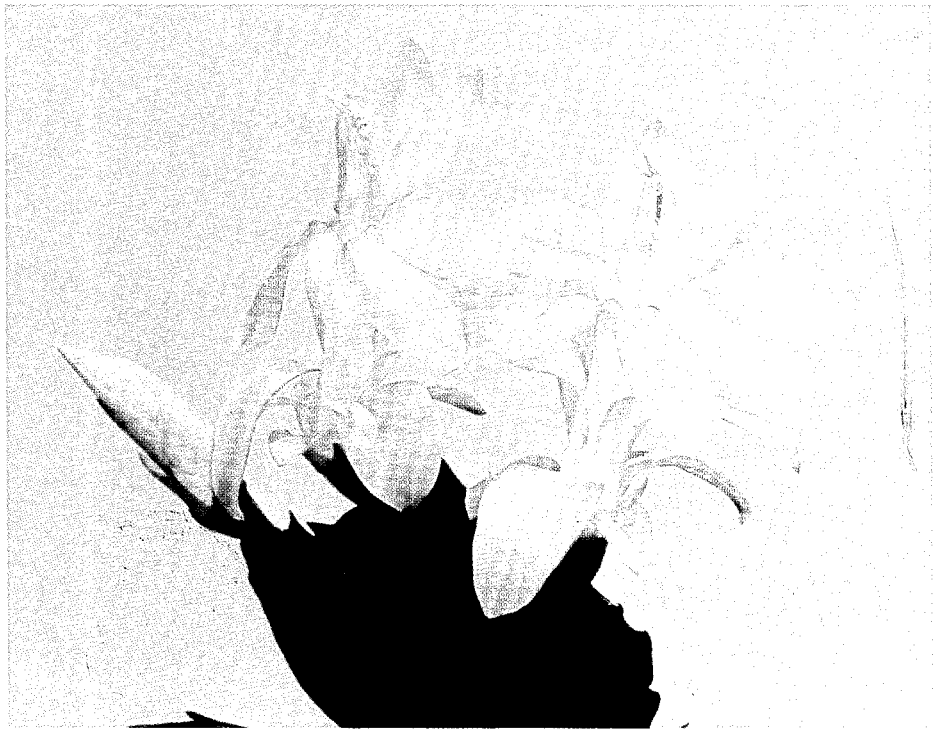

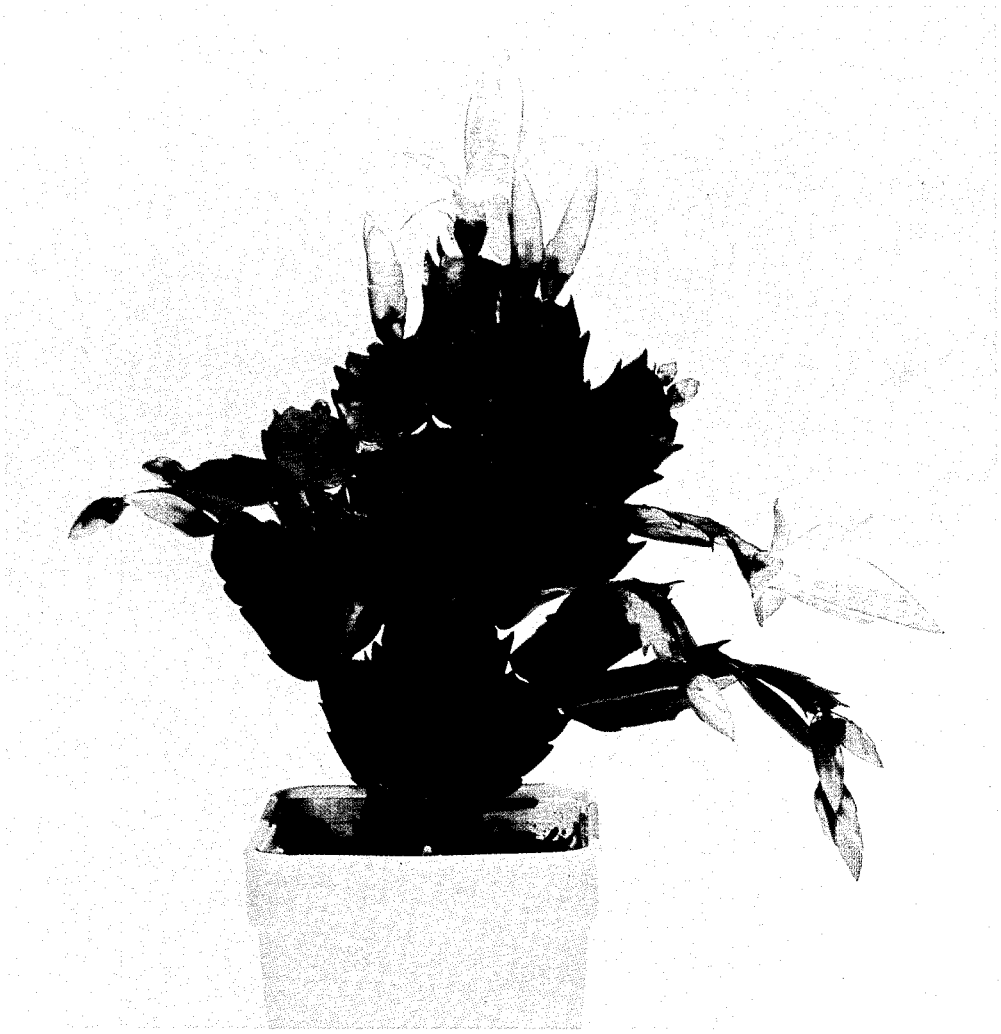

Cobia et al.

[11] Plant 4,200

[45] Jan. 24, 1978

[54] CACTACEAE PLANT

[75] Inventors: Barnell L. Cobia, Winter Garden; Stephen H. Griffith, Apopka, both of Fla.

[73] Assignee: B. L. Cobia, Inc., Winter Garden, Fla.

[21] Appl. No.: 760,352

[22] Filed: Jan. 18, 1976

[51] Int. Cl.[2] ..... A01H 5/00

[52] U.S. Cl. ..... Plt./88

[58] Field of Search ..... Plt./88

*Primary Examiner*—Robert E. Bagwill

*Attorney, Agent, or Firm*—Roger L. Martin

[57] ABSTRACT

A new plant variety of the Cactaceae family is related to the 'Kris Kringle' and 'Lavender Doll' varieties of the *truncatus* species and Zygocactus genus and has a growth habit providing specimens that combine the following principal distinguishing characteristics: a fast growth rate as comparable to that of the 'Kris Kringle' variety; a natural tendency to branch without inducement by pruning during the growth period prior to blooming and which is comparable to that of the 'Kris Kringle' variety; resistances to nutrient deficiencies and fungus type diseases that are comparable to those of the 'Kris Kringle' and 'Lavender Doll' varieties; a substantially greater resistance to flower bud abscission in comparison to the 'Lavender Doll' and 'Kris Kringle' varieites; and a bloom with less recurve in the tube forming tepals in comparison to the 'Kris Kringle' variety and which commonly occurs from about 2 to 4 weeks earlier than blooms of the 'Peach Parfait' variety, and having a bloom life of from about 6 to 9 days, a shorter style and perianth tube than those of the 'Kris Kringle' and 'Lavender Doll' varieties and perianth tube laminating and forming tepals with marginal blade areas that in color are dominated by pink, yellowish pink, red and/or reddish orange hues.

2 Drawing Figures

The invention relates to a new and distinct plant variety of the Cactaceae family and which has been named the *Zygocactus truncatus* 'Twilight Tangerine' by the inventors.

Certain plant varieties of the Cactaceae family are well known in the foliage plant market and among these is the *Zygocactus truncatus* variety commonly known as the 'Christmas Cheer' variety. This variety and its related varieties tend to bloom in the months of November and December in the Northern Hermisphere and hence their appearance in the retail market area is primarily during the Thanksgiving and Christmas seasons.

The 'Christmas Cheer' variety has what may be called a "salmon" color and among its descendants are the varieties of the *truncatus* species which have been named the 'Lavender Doll', 'Kris Kringle' and 'Peach Parfait'.

The 'Lavender Doll' variety has a generally "purplish" colored bloom and its characteristics are set forth in U.S. Plant Pat. No. 3,690. The 'Kris Kringle' variety, on the other hand, has a generally "reddish" colored bloom and its characteristics are generally set forth in U.S. Plant Pat. No. 3,688. The 'Peach Parfait' variety has a generally "salmon" colored bloom and its characteristics are generally set forth in U.S. Plant Pat. No. 3,693. All of these patented varieties have a more upright, compact appearance than specimens of the 'Christmas Cheer' variety.

A general objective of the invention has been to develop a variety of the Catcaceae family which preserves or improves upon characteristics found in specimens of the 'Kris Kringle', 'Lavender Doll' and 'Peach Parfait' varieties and has a "salmon" colored bloom but which nevertheless blooms earlier than specimens of the 'Peach Parfait' variety.

The objectives of the invention have been fully realized by the development of the new plant variety hereinafter described in detail. The new plant variety was developed in a nursery located at Winter Garden, Fla., as a hybrid secured by cross pollinating the flower of a plant specimen of a variety developed by the inventors from a vegetative mutation that appeared on a specimen of the 'Lavender Doll' variety with pollen from a plant specimen of the 'Kris Kringle' variety. The seeds taken from the fertilized seed pod were cultivated at the mentioned nursery location and after prolonged observation of the seedlings, the hybridized plant of the new plant variety was selected and asexually reproduced by the inventors at the Winter Garden nursery through the propagation of stem cuttings taken from the original hybrid plant. The maternal plant variety is a research variety that has not appeared on the market. The variety generally resembles the 'Lavender Doll' variety except that it has slightly larger phylloclades and flower blooms and it exhibits poorer natural tendencies to branch without inducement by pruning during the growth period prior to blooming so that it has a less compact appearance in comparison to the 'Lavender Doll' variety.

Through successive propagations, it has been ascertained that specimens of the new plant variety generally resemble the parent varieties but are distinguishable from these varieties and from other related varieties known to the inventors by a growth habit which is evident in plant specimens propagated and grown under nursery conditions utilized in the growing of tropical plants at Winter Garden, Fla., as combining the following principal characteristics:

1. A fast growth rate that is comparable to that of the 'Kris Kringle' variety,

2. A natural tendency to branch without inducement by pruning during the growth period prior to blooming and which is comparable to that of the 'Kris Kringle' variety, 3. Resistances to nutrient deficiencies and fungus type diseases which are comparable to those of the 'Kris Kringle' and 'Lavender Doll' varieties, 4. Substantially greater resistance to flower bud abscission as compared to that exhibited by the 'Lavender Doll' and 'Kris Kringle' varieties, and 5. A bloom exhibiting less recurve in the tube forming tepals in comparison to the 'Kris Kringle' variety and which commonly occurs from about 2 to 4 weeks earlier than blooms of the 'Peach Parfait' variety, and has a. a bloom life of from about 6 to about 9 days, b. a shorter style and perianth tube than those of the 'Kris Kringle' and 'Lavender Doll' varieties, and perianth tube laminating and forming tepals with marginal blade areas that in color are dominated by pink, purplish pink, yellowish pink, red and/or reddish orange hues.

The accompanying drawings serve by color photographic means to illustrate the new plant variety and wherein one sheet shows a 6 month old specimen of the new plant variety that was propagated in the month of June, and the other sheet illustrates an 11 month old specimen of the new plant variety that was propagated in the month of January and pruned to one tier above the original cutting the following June, and blooms and maturing buds of the new variety.

The following is a detailed description of the new plant variety with colors and hues, unless otherwise clearly indicated by the text through the absence of color notations, being named in accord with the ISCC-NBS Method of designating colors, (U.S. Department of Commerce, National Bureau of Standards, Circular 553, issued Nov. 1, 1955) the named colors being interpreted from color notations derived by comparison with the color specimens in the current "Neighboring Hues Edition" of the Munsell Book of Color, published by the Munsell Color Company, Inc., of Baltimore, Md. The description is further based on observations of well fertilized plants of less than one (1) year of age from initial propagation and which were grown under 50–75% shaded glasshouse nursery conditions in the Winter Garden, Fla., area and wherein temperatures range from 60°–85° F. during the winter months, and from 75°–95° F. during the summer months, and are ambient during the intervening periods.

DETAILED PLANT DESCRIPTION

Name: *Zygocactus truncatus* 'Twilight Tangerine'.

Parentage:

*Maternal.*—Unnamed and unmarketed variety generally resembling the *Zygocactus truncatus* 'Lavender Doll' variety but with slightly larger phylloclades and blooms and with poorer natural branching characteristics than exhibited by the 'Lavender Doll' variety.

*Paternal.*—*Zygocactus truncatus* 'Kris Kringle'.

Classification:

*Botanic* (*Britton and Rose, The Cactaceae, Constable and Co., Ltd., London 1937, Vol. IV).*—

| | | |
|---|---|---|
| (1) | Family: | *Cactaceae* |
| (2) | Tribe: | *Cereeae* |
| (3) | Sub-tribe: | *Epiphyllanae* |
| (4) | Genus: | *Zygocactus* |
| (5) | Species: | *Truncatus (Haworth) Schumann* |

*Commercial.*—Thanksgiving-Christmas blooming cactus.

Form: Terrestrial, shade loving, succulent, leafless plant with jointed and branched stems.

Stems:

*General.*—Irregular with usually multichotomous branching of both upright and pendulous, adventitiously rootable, flattened phylloclades that have a prominent midrib and prominently toothed lateral wings.

*Phylloclades.*—General: Elongated and flat with transversely elongated, aerole bearing, truncated apex, with inwardly tapering basal wing margins that merge through a broad, usually pointed basal juncture with the phylloclades therebelow, and with an axially areole associated with each tooth. Midrib: General — Extends longitudinally of phylloclade and continuously through joints with laterally tapering cortex at wing insertions. Pith surrounding vascular bundles that branch and provide lateral extensions of the vascular system to the marginal teeth. Texture — Smooth, waxy epidermis with wax in small embedded scales and becoming corky in basal stem areas with age. Size (2–6 months old) — Length: Usually between 35 and 55 mm. with the average for respective plant specimens being usually between 39 and 49 mm. Thickness: Usually between 2 and 6 mm.with the average for respective plant specimens being usually between 2 and 4 mm. Color (at maturity) — Commonly moderate yellow green (5 GY 6/6) (5 GY 6/4) (5 GY 5/6) (near 5 GY 5/4) (7.5 GY 5/4) and/or moderate olive green (5 GY 4/4) (7.5 GY 4/4). Wings: General shape — Generally flattened from midrib cortex to tooth insertions with slight thinning taper toward margins and tendency toward undulation of margins. Margins — Toothed (modified leaves). Texture — Succulent to leathery with smooth, waxy epidermis having wax arranged in small embedded scales and becoming corky in basal plant areas with age. Size (2–6 months old) — Center thickness: Usually between 1 and 2.2 mm. Width (as measured from phylloclade axis to most offset lateral areole): Usually between 7 and 19 mm. Color (at maturity) — Commonly moderate yellow green (5 GY 6/6) (5 GY 6/4) (5 GY 5/6) (near 5 GY 5/4) (7.5 GY 5/4) and/or moderate olive green (5 GY 4/4) (7.5 GY 4/4). Teeth: General shape — Generally flattened and tapered along margins from wing insertions to an apex having a hyaline, single cell, pointed spine with nonpredictable bending. Adaxial marginal shape: Usually straight to slightly concave. Abaxial marginal shape: Irregular with tendencies toward a medial indentation that provides a distal terminus for a convex proximal marginal edge portion, and a basal terminus for a distal marginal edge portion that varies from straight to convex. Orientation — Usually projects distally of phylloclade base in an alternate arrangement. Margins — Entire. Texture — Succulent to leathery with smooth waxy epidermis having wax in small embedded scales and becoming corky in basal plant areas with age. Number — Usually from 6 to 8 per phylloclade. Size (2–6 months old) — Center thickness: Usually between 0.5 and 2 mm. Areole to apex dimension (adaxial marginal side): Usually between 2 and 8 mm. for teeth located distally of basal teeth. Color (at maturity) — Commonly moderate yellow green (5 GY 6/6) (5 GY 6/4) (5 GY 5/6) (near 5 GY 5/4) (7.5 GY 5/4)

and/or moderate olive green (5 GY 4/4) (7.5 GY 4/4). Areoles: Terminal areole — Large, elongated, oval-shaped with several acicular bristles, copious multi-cellular hairs, and several buds that may mature into either new phylloclades or flowers. The opposite ends of the areole are located adjacent to subsidiary areoles which are in turn located at the axils of teeth that are located at the distal end of the phylloclade. Axillary areoles — A few acicular bristles without glochidia but having relatively few short, brownish to colorless, multi-cellular hairs. In areoles that are located below the teeth at the distal end of the phylloclade, there is usually only one bud which is frequently latent.

Buds: Unarmored, ovid and chlorophyllous.

Flowers:

*General.*—Sessile, zygomorphic, usually solitary, terminal, perfect and epigynous with double hypanthium and tepals (undifferentiated whorled sepals and petals) having a spiral emergence as a perianth provided with a sepaloid series of free tepals, a tube laminating series of tepals, and a tube forming series of united tepals.

*Sepaloid series.*—General: Free tepals inserted on top of ovary. Shape: Deltoid in outer members of whorl and grading inwardly in the whorl to tepals which are elliptic in shape. Tips are generally acute with some acuminate tendencies. Margins are entire with sparse irregular teeth appearing mainly in apex areas of the inner members of the whorl. Texture: Succulent and glabrous outer whorl members and grading inwardly in the whorl to silken blades with fleshy basal areas. Number: Usually from 8 to 10. Size (at full bloom): Base-tip dimension — Usually less than 32 mm. Maximum width dimension — Usually less than 16 mm. Color: Outer whorl members usually have a continuous field and color is dominated by a yellow green hue. Inner whorl members usually have a translucent white basal area that merges with marginal blade areas which in color are dominated by pink, purplish pink, yellowish pink, red and/or reddish orange hue. Commonly light yellow green (2.5 GY 8/6) (near 2.5 GY 8/4) (5 GY 8/6) (near 5 GY 8/4), moderate yellow green (2.5 GY 7/6) (2.5 GY 7/4) (2.5 GY 6/6) (2.5 GY 6/4) (5 GY 7/6) (5 GY 7/4) (near 5 GY 6/6) (near 5 GY 6/4) and/or strong yellow green (2.5 GY 6/8) (5 GY 6/8) in continuous field of outer whorl members. Commonly light pink (near 10 RP 8/6), moderate pink (near 10 RP 8/6) (10 RP 7/6) (near 5 R 7/6) (2.5 R 7/6) strong pink (10 RP 7/8) (2.5 R 7/8), deep pink (near 5 R 6/8) (2.5 R 6/10) (2.5 R 6/8) (2.5 R 6/10) (near 2.5 R 6/8) (5 R 6/10) (5 R 6/8), dark pink (near 5 R 6/6) (10 RP 6/6), light purplish pink (5 RP 8/6), moderate purplish pink (near 7/5 RP 7/8) (near 5 RP 7/8), deep purplish pink (7.5 RP 6/10), dark purplish pink (7.5 RP 6/8) (7.5 RP 6/6), strong yellowish pink (5 R 7/8), dark yellowish pink (7.5 R 6/6), moderate red (5 R 5/10) (5 R 5/8), and/or moderate reddish orange (7.5 R 6/10) (7.5 R 6/8) (7.5 R 5/10) (near 7.5 R 5/8) in marginal areas of inner whorl members merging with a translucent white basal area. Orientation at full bloom: Varying inwardly in the whorl from erect to recurve.

*Tube laminating series.*—General: Tepals inserted on ovary and basally united below the throat as outer laminations on the perianth tube and with progressively greater amounts of basal fusion inwardly in the whorl. Shape: Grading inwardly in the whorl with progressively longer base-tip dimensions and with elliptic blades with some oblanceolate tendencies and long acute tips. Entire margins with sparse, irregular teeth mainly in apex areas. Texture: Succulent, slightly fleshy, basal areas with silken blades. Number: Usually 4 or 5. Size (at full bloom): Base-tip dimension — Usually between 25 and 52 mm. Maximum width dimension — Usually between 12 and 17 mm. Color: Marginal areas are in color dominated by pink, purplish pink, yellowish pink, red and/or reddish orange hues that merge with a translucent white basal area. Commonly light pink (near 10 RP 8/6), moderate pink (near 10 RP 8/6), strong pink (10 RP 7/8), deep pink (near 10 RP 6/8) (5 R 6/10), dark pink (near 10 RP 6/6), light purplish pink (near 10 RP 8/6), moderate purplish pink (7.5 RP 7/8), dark purplish pink (7.5 RP 6/8) (7.5 RP 6/6) (5 RP 6/8) (5 RP 6/6), moderate red (5 R 5/10) ( b 5 R 5/8), moderate reddish orange (near 7.5 6/10) (7.5 R 6/8) (7.5 R 5/10) (7.5 R 5/8) and/or dark yellowish pink (near 7.5 R 6/6) in marginal areas and merging with translucent white basal areas. Orientation at full bloom: Acute to recurve.

*Tube forming series.*—General: Tepals basally united to form hollow perianth tube that is inserted on ovary and equipped with irregular carina (keel) at throat. Shape: Perianth tube — Elongated and ellipsoidal in cross section. Blades — Nearly zygomorphic and lanceolate with acute tips. Entire margins with sparse, irregular teeth mainly in apex areas. Carina (keel) — Transcending and irregular. Texture: Perianth tube — Thick, succulent and slightly ribbed. Blades — Translucent and silken. Carina (keel) — Fleshy. Blade Number: Usually 8 or 9. Size (at full bloom): Perianth tube — Base to keel length: Usually between 24 and 30 mm. along axis of tube with average length differences between measurements along dorsal and ventral sides for respective specimens usually being between 2 and 6 mm. Internal Major Axis (at throat): Usually between 6 and 11 mm. when measured perpendicular to axis at perianth tube. Internal Minor Axis (at throat): Usually between 4 and 8 mm. when measured perpendicular to axis of perianth tube. Blades — Length (keel to tip): Usually between 22 and 36 mm. Width (maximum): Usually between 8 and 16 mm. Color (at full bloom): Perianth tube — Translucent white with overtones of color usually dominated by purplish pink and/or pink hues commonly purplish white (5 RP 9/1), pale purplish pink (10 P 8/4) (2.5 RP 8/4) (5 RP 9/2) (5 RP 8/4) (5 RP 8/2) (7.5 RP 8/4), light purplish pink (5 RP 8/6), light pink (near 10 RP 8/4) and/or moderate pink (near 10 RP 8/4) in overtone. Blades — Marginal blade area with color dominated by pink, purplish pink, yellowish pink, red and/or reddish orange hues and merging with translucent white basal areas. Commonly dark pink (10 RP 6/6) (near 5 R 6/6), deep pink (near 10 RP 6/10) (10 RP 6/8) (5 R 6/10) (5 R 6/8) (2.5 R 6/10) (2.5 R 6/8), strong pink (10 RP 7/8) (2.5 R 7/8), dark purplish pink (near 7.5 RP 6/8), strong yellowish pink (near 5 R 7/8), moderate red (near 5 R 5/10) (5 R 5/8), and/or moderate reddish orange (near 10 R 6/8) (7.5 R 6/10) (7.5 R 6/8) (near 7.5 R 5/10) (7.5 R 5/8). Carina (keel) — Commonly strong reddish purple (near 10 P 4/10) (2.5 RP 4/10) and/or deep reddish purple (near 10 P 3/10) (near 10 P 3/8) (2.5 RP 3/10) (near 2.5 RP 3/8). Orientation (at full bloom): Erect to recurve.

*Androecium* (*stamens*).—General: Numerous exserted and diadelphous stamens with one group having filaments basally fused to the perianth tube and the other group having filaments basally united to form a nectary housing, thin annulus around the style which is provided with a thin, deflexed, irregularly toothed margin or ruffle at the throat of the annulus. Stamen Number: Tube attached group — Usually between 89 and 95. Basally united group — Usually between 17 and 23. Filaments: General — Translucent and glabrous with anther connective. Shape — Long, slender and terete. Texture — Glabrous and silken. Color — Translucent white. Size (at full bloom) — Length: Tube attached group — Usually between 32 and 47 mm. Basally united group — Usually between 36 and 47 mm. Diameter: Usually between 0.2 mm and 0.3 mm. intermediate the opposite ends. Anthers: General — Adnate with four longitudinally dehiscent pollen sacs. Shape — Elongated. Texture — Waxy. Color (post dehiscence) — Commonly light greenish yellow (10 Y 9/6) (near 7.5 Y 9/8) (near 7.5 Y 9/6), brilliant greenish yellow (near (7.5 Y 9/8) and/or light yellow (5 Y 9.6).

*Gynoecium* (*pistil*).—General: Compound, pariental placentation with united style surrounded by annular diffuse nectary at its insertion. Style: General — Stout and inserted in ovary. Shape — Elongated and terete. Texture — Fleshy and glabrous with short inner glutinous hairs at distal end. Color — Commonly strong reddish purple (2.5 RP 5/10), moderate reddish purple (10 RP 4/10), deep purplish pink (5 RP 6/10) and/or moderate purplish red (5 RP 5/8) (near 7.5 RP 4/8). Size (at full bloom) —Length: Usually between 51 and 55 mm. Diameter: Usually between 0.8 and 1.0 mm. intermediate the opposite ends. Stigma: General — Exserted and erect with usually 6 or 7 inner marginally adhering lobes. Shape — Elongated and tapered toward lobe tips and having relatively blunt apices. Texture — Fleshy and smooth with short glutinous hairs. Color — Commonly strong reddish purple (10 P 5/10) (2.5 RP 5/10) (near 2.5 RP 4/10) and/or moderate reddish purple (near 10 P 5/8) (2.5 RP 5/8) (near 2.5 RP 5/6). Size (lobe length at full bloom) — Usually between 3.5 and 5.2 mm. Ovary: General — Epigynous with thin epidermis and distally located concavity and with a single cavity having 6 or 7 carpels with numerous ovules. Shape — Terete to ovid and generally broadening from insertion to floral end and externally ribbed. Texture — Succulent and glabrous with thin outer epidermis. Color — Commonly light yellow green (5 GY 8/6) (near 5 GY 8/4) (2.5 GY 8/6) (near 2.5 GY 8/4), moderate yellow green (near 5 GY 7/6) (5 GY 6/6) (5 GT 5/5) (2.5 GY 7/6) (2.5 GY 6/6) and/or strong yellow green (2.5 GY 6/8). Size (at full bloom) — Length (insertion to concavity base): Usually between 9 and 11 mm. Major Axis (distal end of concavity): Usually between 7 and 10 mm. Minor Axis (distal end of concavity): Usually between 6 and 9 mm.

Growing characteristics: A fast growth rate that is comparable to that of the 'Kris Kringle' variety with an upright and compact appearance as evidenced by erect stems with heavy (frequent) branching with or without pruning, and a natural tendency to branch without inducement by pruning during the growth period prior to blooming and which is comparable to that of the 'Kris Kringle' variety. Good resistances to nutrient deficiencies and fungus type diseases and which are comparable to those of the 'Kris Kringle' and 'Lavender Doll' varieties and a substantially greater resistance to flower bud abscission in comparison to the 'Lavender Doll' and 'Kris Kringle' varieties. Generally less recurve in the tube forming tepals as compared to specimens of the 'Kris Kringle' variety and with a bloom life (from initial tepal separation to initial tepal withering) from about 6 to about 9 days.

The following is a general description of a specimen of the new plant variety that was grown from the propagation of a single phylloclade in a nursery at Winter Gardens, Fla.

Age of plant: 6 months from initial propagation.
Branches from propagated cuttings: 4.
Total number of phylloclades grown from cutting: 23.
General:

| Branch No. | No. of Phylloclades | Max. Length | No. of Tips |
|---|---|---|---|
| 1 | 6 | 142 mm. | 3 |
| 2 | 6 | 126 mm. | 3 |
| 3 | 5 | 148 mm. | 2 |
| 4 | 6 | 127 mm. | 3 |

Midribs:

| Branch No. | Length (avg.) | Thickness (avg.) |
|---|---|---|
| 1 | 47 mm. | 3.6 mm. |
| 2 | 42 mm. | 3.2 mm. |
| 3 | 40 mm. | 3.6 mm. |
| 4 | 41 mm. | 3.0 mm. |

Wings:

| Branch No. | Center Thickness (avg.) | Max. Width (avg.) |
|---|---|---|
| 1 | 1.6 mm. | 14 mm. |
| 2 | 1.7 mm. | 12 mm. |
| 3 | 1.8 mm. | 14 mm. |
| 4 | 1.6 mm. | 12 mm. |

Teeth:

| Branch No. | No./Phylloclades (Avg.) | Center Thickness | Areole to Apex Dimension (avg.) |
|---|---|---|---|
| 1 | 7 | 1.23 mm. | 4.1 mm. |
| 2 | 6 | 1.0 mm. | 3.3 mm. |

-continued

| Branch No. | No./Phylloclades (Avg.) | Center Thickness | Areole to Apex Dimension (avg.) |
|---|---|---|---|
| 3 | 7 | 1.1 mm. | 4.8 mm. |
| 4 | 6 | .85 mm. | 3.9 mm. |

Phylloclade color: Moderate yellow green (5 GY 6/6) (5 GY 6/4) (7.5 GY 5/4).

The following is a general description of a flower of the new plant variety which bloomed in December on a plant grown under shaded glasshouse nursery conditions in Winter Garden, Fla.

Bloom life: 8 days.

Sepaloid series of tepals:

*Number.*—10.

*Size (at full bloom).*—Maximum base-tip dimension: 21 mm. Minimum base-tip dimension: 3 mm. Maximum width dimension: 12 mm.

*Color.*—Moderate yellow green (2.5 GY 7/6) (2.5 GY 7/4) in field of outer members. Moderate red (5 R 5/10) and moderate reddish orange (7.5 R 6/10) (7.5 R 6/8) in marginal blade areas and merging with translucent white basal areas.

Tube laminating series:

*Number.*—5.

*Size (at full bloom).*—Maximum base-tip dimension: 42 mm. Minimum base-tip dimension: 26 mm. Maximum width dimensions: 14 mm. Minimum width dimension: 13 mm.

*Color.*—Moderate red (5 R 5/10) in marginal area and merging with a translucent white basal area.

Tube forming series of tepals:

*Number.*—9.

*Size (at full bloom).*—Perianth tube: Base to keel length — 25 mm. Interior major axis (at throat) — 8 mm. Interior minor axis (at throat) — 6 mm. Blades: Maximum length (keel to tip) — 26.5 mm. Minimum length (keel to tip) — 24 mm. Maximum width — 13 mm. Minimum width — 9 mm.

*Color.*—Perianth tube: Translucent white with overtone of pale purplish pink (10 P 8/4) (2.5 RP 8/4). Blades: Moderate reddish orange (7.5 R 6/10) in marginal areas and merging with translucent white basal area. Carina (keel): Deep reddish purple (2.5 RP 3/10).

Androecium:

*Stamen number.*—Tube attached group: 94. Basally united group: 22.

*Filaments.*—Color: Translucent white. Size (at full bloom): Length — Tube attached group: 38.5 mm. (avg.). Basally united group: 41 mm. (avg.). Diameter — 0.25 mm. intermediate the opposite ends.

*Anthers.*—Color (post dehiscence): Light greenish yellow (10 Y 9/6) (near 7.5 Y 9/8).

Gynoecium (pistil):

*Style.*—Color: Moderate reddish purple (10 RP 4/10). Size (at full bloom): Length — 52 mm. Diameter — 0.9 mm. intermediate the opposite ends.

*Stigma.*—Color: Strong reddish purple (2.5 RP 5/10) (10 P 5/10). Size: Lobe length about 4 mm.

*Ovary.*—Color: Moderate yellow green (5 GY 6/6) (5 GY 5/6) (2.5 GY 6/6). Size (at full bloom) — Length (insertion to concavity base) — 10 mm. Major axis (distal end of concavity) — 9 mm. Minor axis (distal end of concavity) — 8 mm.

We claim:

1. The new and distinct variety of the Cactaceae family substantially as herein shown and described and which has a growth habit providing specimens that combine the following principal distinguishing characteristics:

1. A fast growth rate as comparable to that of the 'Kris Kringle' variety,
2. A natural tendency to branch without inducement by pruning during the growth period prior to blooming and which is comparable to that of the 'Kris Kringle' variety,
3. Resistances to nutrient deficiencies and fungus type diseases that are comparable to those of the 'Kris Kringle' and 'Lavender Doll' varieties,
4. A substantially greater resistance to flower bud abscission in comparison to the 'Lavender Doll' and 'Kris Kringle' varieties, and
5. A bloom with less recurve in the tube forming tepals in comparison to the 'Kris Kringle' variety and which commonly occurs from about 2 to 4 weeks earlier than bloom of the 'Peach Parfait' variety, and having
   a. a bloom life of from about 6 to about 9 days,
   b. a shorter style and perianth tube than those of the 'Kris Kringle' and 'Lavender Doll' varieties, and
   c. perianth tube laminating and forming tepals with marginal blade areas that in color are dominated by pink, purplish pink, yellowish pink, red and/or reddish orange hues.

* * * * *

UNITED STATES PATENT OFFICE

CERTIFICATE OF CORRECTION

Patent No. Plant 4,200 Dated January 24, 1978

Inventor(s) Barnell L. Cobia, et al

It is certified that error appears in the above-identified patent and that said Letters Patent are hereby corrected as shown below:

Delete Columns 1 thru 10 and substitute the attached Columns 1 thru 10 therefore.

Signed and Sealed this

*Sixteenth* Day of *January 1979*

[SEAL]

*Attest:*

RUTH C. MASON
*Attesting Officer*

DONALD W. BANNER
*Commissioner of Patents and Trademarks*

CACTACEAE PLANT

The invention relates to a new and distinct plant variety of the Cactaceae family and which has been named the *Zygocactus truncatus* 'Twilight Tangerine' by the inventors.

Certain plant varieties of the Cactaceae Family are well known in the foliage plant market and among these is the *Zygocactus truncatus* variety commonly known as the 'Christmas Cheer' variety. This variety and its related varieties tend to bloom in the months of November and December in the Northern Hemisphere and hence their appearance in the retail market area is primarily during the Thanksgiving and Christmas seasons.

The 'Christmas Cheer' variety has what may be called a "salmon" color and among its descendants are the varieties of the *truncatus* species which have been named the 'Lavender Doll', 'Kris Kringle' and 'Peach Parfait'.

The 'Lavender Doll' variety has a generally "purplish" colored bloom and its characteristics are set forth in U.S. Plant Pat. No. 3,690. The 'Kris Kringle' variety, on the other hand, has a generally "reddish" colored bloom and its characteristics are generally set forth in U.S. Plant Pat. No. 3,688. The 'Peach Parfait' variety has a generally "salmon" colored bloom and its characteristics are generally set forth in U.S. Plant Pat. No. 3,693. All of these patented varieties have a more upright, compact appearance than specimens of the 'Christmas Cheer' variety.

A general objective of the invention has been to develop a variety of the Cactaceae family which preserves or improves upon characteristics found in specimens of the 'Kris Kringle', 'Lavender Doll' and 'Peach Parfait' varieties and has a "salmon" colored bloom but which nevertheless blooms earlier than specimens of the 'Peach Parfait' variety.

The objectives of the invention have been fully realized by the development of the new plant variety hereinafter described in detail. The new plant variety was developed in a nursery located at Winter Garden, Fla., as a hybrid secured by cross pollinating the flower of a plant specimen of a variety developed by the inventors from a vegetative mutation that appeared on a specimen of the 'Lavender Doll' variety with pollen from a plant specimen of the 'Kris Kringle' variety. The seeds taken from the fertilized seed pod were cultivated at the mentioned nursery location and after prolonged observation of the seedlings, the hybridized plant of the new plant variety was selected and asexually reproduced by the inventors at the Winter Garden nursery through the propagation of stem cuttings taken from the original hybrid plant. The maternal plant variety is a research variety that has not appeared on the market. The variety generally resembles the 'Lavender Doll' variety except that it has slightly larger phylloclades and flower blooms and it exhibits poorer natural tendencies to branch without inducement by pruning during the growth period prior to blooming so that it has a less compact appearance in comparison to the 'Lavender Doll' variety.

Through successive propagations, it has been ascertained that specimens of the new plant variety generally resemble the parent varieties but are distinguishable from these varieties and from other related varieties known to the inventors by a growth habit which is evident in plant specimens propagated and grown under nursery conditions utilized in the growing of tropical plants at Winter Garden, Fla., as combining the following principal characteristics:

1. A fast growth rate that is comparable to that of the 'Kris Kringle' variety,
2. A natural tendency to branch without inducement by pruning during the growth period prior to blooming and which is comparable to that of the 'Kris Kringle' variety,
3. Resistances to nutrient deficiencies and fungus type diseases which are comparable to those of the 'Kris Kringle' and 'Lavender Doll' varieties,
4. Substantially greater resistance to flower bud abscission as compared to that exhibited by the 'Lavender Doll' and 'Kris Kringle' varieties, and
5. A bloom exhibiting less recurve in the tube forming tepals in comparison to the 'Kris Kringle' variety and which commonly occurs from about 2 to 4 weeks earlier than blooms of the 'Peach Parfait' variety, and has
   a. a bloom life of from about 6 to about 9 days,
   b. a shorter style and perianth tube than those of the 'Kris Kringle' and 'Lavender Doll' varieties, and perianth tube laminating and forming tepals with marginal blade areas that in color are dominated by pink, purplish pink, yellowish pink, red and/or reddish orange hues.

The accompanying drawings serve by color photographic means to illustrate the new plant variety and wherein one sheet shows a six month old specimen of the new plant variety that was propagated in the month of June, and the other sheet illustrates an eleven month old specimen of the new plant variety that was propagated in the month of January and pruned to one tier above the original cutting the following June, and blooms and maturing buds of the new variety.

The following is a detailed description of the new plant variety with colors and hues, unless otherwise clearly indicated by the text through the absence of color notations, being named in accord with the ISCC-NBS Method of designating colors, (U.S. Department of Commerce, National Bureau of Standards, Circular 553, issued Nov. 1, 1955) the named colors being interpreted from color notations derived by comparision with the color specimens in the current "Neighboring Hues Edition" of the Munsell Book of Color, published by the Munsell Color Company, Inc., of Baltimore, Md. The description is further based on observations of well fertilized plants of less than 1 year of age from initial propagation and which were grown under 50–75% shaded glasshouse nursery conditions in the Winter Garden, Fla., area and wherein temperatures range from 60°–85° F. during the winter months, and from 75°–95° F. during the summer months, and are ambient during the intervening periods.

DETAILED PLANT DESCRIPTION

Name: *Zygocactus truncatus* 'Twilight Tangerine'.

Parentage:

A. *Maternal.*—Unnamed and unmarketed variety generally resembling the *Zygocactus truncatus* 'Lavender Doll' variety but with slightly larger phylloclades and blooms and with poorer natural branching characteristics than exhibited by the 'Lavender Doll' variety.

B. *Paternal.*—*Zygocactus truncatus* 'Kris Kringle'.

Classification:

A. *Botanic.*—(Britton and Rose, *The Cactaceae,* Constable and Co., Ltd., London 1937, Vol. IV)—

| | |
|---|---|
| (1) Family: | Cactaceae |
| (2) Tribe: | Cereeae |
| (3) Sub-tribe: | Epiphyllanae |
| (4) Genus: | Zygocactus |
| (5) Species: | *truncatus* (Haworth) Schumann |

B. *Commercial.*—Thanksgiving-Christmas blooming cactus.

Form: Terrestrial, shade loving, succulent, leafless plant with jointed and branched stems.

Stems:

A. *General.*—Irregular with usually multichotomous branching of both upright and pendulous, adventitiously rootable, flattened phylloclades that have a prominent midrib and prominently toothed lateral wings.

B. *Phylloclades.*—[1] General: Elongated and flat with transversely elongated, areole bearing, truncated apex, with inwardly tapering basal wing margins that merge through a broad, usually pointed basal juncture with the phylloclade therebelow, and with an axillary areole associated with each tooth. [2] Midrib: (a) General — Extends longitudinally of phylloclade and continuously through joints with laterally tapering cortex at wing insertions. Pith surrounding vascular bundles that branch and provide lateral extensions of the vascular system to the marginal teeth. (b) Texture — Smooth, waxy epidermis with wax in small embedded scales and becoming corky in basal stem areas with age. (c) Size (2–6 months old) — (1) Length: Usually between 35 and 55 mm. with the average for respective plant specimens being usually between 39 and 49 mm. (2) Thickness: Usually between 2 and 6 mm. with the average for respective plant specimens being usually between 2 and 4 mm. (d) Color (at maturity) — Commonly moderate yellow green (5 GY 6/6) (5 GY 6/4) (5 GY 5/6) (near 5 GY 5/4) (7.5 GY 5/4) and/or moderate olive green (5 GY 4/4) (7.5 GY 4/4). [3] Wings: (a) General shape — Generally flattened from midrib cortex to tooth insertions with slight thinning taper toward margins and tendency toward undulation of margins. (b) Margins — Toothed (modified leaves). (c) Texture — Succulent to leathery with smooth, waxy epidermis having wax arranged in small embedded scales and becoming corky in basal plant areas with age. (d) Size (2–6 months old) — (1) Center thickness: Usually between 1 and 2.2 mm. (2) Width (as measured from phylloclade axis to most offset lateral areole): Usually between 7 and 19 mm. (e) Color (at maturity) — Commonly moderate yellow green (5 GY 6/6) (5 GY 6/4) (5 GY 5/6) (near 5 GY 5/4) (7.5 GY 5/4) and/or moderate olive green (5 GY 4/4) (7.5 GY 4/4). [4] Teeth: (a) General shape — Generally flattened and tapered along margins from wing insertions to an apex having a hyaline, single cell, pointed spine with non-predictable bending. (1) Adaxial marginal shape: Usually straight to slightly concave. (2) Abaxial marginal shape: Irregular with tendencies toward a medial indentation that provides a distal terminus for a convex proximal marginal edge portion, and a basal terminus for a distal marginal edge portion that varies from straight to convex. (b) Orientation — Usually projects distally of phylloclade base in an alternate arrangement. (c) Margins — Entire. (d) Texture — Succulent to leathery with smooth waxy epidermis having wax in small embedded scales and becoming corky in basal plant areas with age. (e) Number — Usually from 6 to 8 per phylloclade. (f) Size (2–6 months old) — (1) Center thickness: Usually between 0.5 and 2 mm. (2) Areole to apex dimension (adaxial marginal side): Usually between 2 and 8 mm. for teeth located distally of basal teeth. (g) Color (at maturity) — Commonly moderate yellow green (5 GY 6/6) (5 GY 6/4) (5 GY 5/6) (near 5 GY 5/4) (7.5 GY 5/4) and/or moderate olive green (5 GY 4/4) (7.5 GY 4/4). [5] Areoles: (a) Terminal areole — Large, elongated, oval-shaped with several acicular bristles, copious multi-cellular hairs, and several buds that may mature into either new phylloclades or flowers. The opposite ends of the areole are located adjacent to subsidiary areoles which are in turn located at the axils of teeth that are located at the distal end of the phylloclade. (b) Axillary areoles — A few acicular bristles without glochidia but having relatively few short, brownish to colorless, multi-cellular hairs. In areoles that are located below the teeth at the distal end of the phylloclade, there is usually only one bud which is frequently latent.

Buds: Unarmored, ovid and chlorophyllous.

Flowers:

A. *General.*—Sessile, zygomorphic, usually solitary, terminal, perfect and epigynous with double hypanthium and tepals (undifferentiated whorled sepals and petals) having a spiral emergence as a perianth provided with a sepaloid series of free tepals, a tube laminating series of tepals, and a tube forming series of united tepals.

B. *Sepaloid series.*—[1] General: Free tepals inserted on top of ovary. [2] Shape: Deltoid in outer members of whorl and grading inwardly in the whorl to tepals which are elliptic in shape. Tips are generally acute with some acuminate tendencies. Margins are entire with sparse irregular teeth appearing mainly in apex areas of the inner members of the whorl. [3] Texture: Succulent and glabrous outer whorl members and grading inwardly in the whorl to silken blades with fleshy basal areas. [4] Number: Usually from 8 to 10. [5] Size (at full bloom): (a) Base-tip dimension — Usually less than 32 mm. (b) Maximum width dimension — Usually less than 16 mm. [6] Color: Outer whorl members usually have a continuous field and color is dominated by a yellow green hue. Inner whorl members usually have a translucent white basal area that merges with marginal blade areas which in color are dominated by pink, purplish pink, yellowish pink, red and/or reddish orange hue. Commonly light yellow green (2.5 GY 8/6) (near 2.5 GY 8/4) (5 GY 8/6) (near 5 GY 8/4), moderate yellow green (2.5 GY 7/6) (2.5 GY 7/4) (2.5 GY 6/6) (2.5 GY 6/4) (5 GY 7/6) (5 GY 7/4) (near 5 GY 6/6) (near 5 GY 6/4) and/or strong yellow green (2.5 GY 6/8) (5 GY 6/8) in continuous field of outer whorl members. Commonly light pink (near 10 RP 8/6), moderate pink (near 10 RP 8/6) (10 RP 7/6) (near 5 R 7/6) (2.5 R 7/6)

strong pink (10 RP 7/8) (2.5 R 7/8), deep pink (near 5 R 6/8) (2.5 R 6/10) (2.5 R 6/8) (2.5 R 6/10) (near 2.5 R 6/8) (5 R 6/10) (5 R 6/8), dark pink (near 5 R 6/6) (10 RP 6/6), light purplish pink (5 RP 8/6), moderate purplish pink (near 7.5 RP 7/8) (near 5 RP 7/8), deep purplish pink (7.5 RP 6/10), dark purplish pink (7.5 RP 6/8) (7.5 RP 6/6), strong yellowish pink (5 R 7/8), dark yellowish pink (7.5 R 6/6), moderate red (5 R 5/10) (5 R 5/8), and/or moderate reddish orange (7.5 R 6/10) (7.5 R 6/8) (7.5 R 5/10) (near 7.5 R 5/8) in marginal areas of inner whorl members merging with a translucent white basal area. [7] Orientation at full bloom: Varying inwardly in the whorl from erect to recurve.

C. *Tube laminating series.*—[1] General: Tepals inserted on ovary and basally united below the throat as outer laminations on the perianth tube and with progressively greater amounts of basal fusion inwardly in the whorl. [2] Shape: Grading inwardly in the whorl with progressively longer base-tip dimensions and with elliptic blades with some oblanceolate tendencies and long acute tips. Entire margins with sparse, irregular teeth mainly in apex areas. [3] Texture: Succulent, slightly fleshy, basal areas with silken blades. [4] Number: Usually 4 or 5. [5] Size (at full bloom): (a) Base-tip dimension — Usually between 25 and 52 mm. (b) Maximum width dimension — Usually between 12 and 17 mm. [6] Color: Marginal areas are in color dominated by pink, purplish pink, yellowish pink, red and/or reddish orange hues that merge with a translucent white basal area. Commonly light pink (near 10 RP 8/6), moderate pink (near 10 RP 8/6), strong pink (10 RP 7/8), deep pink (near 10 RP 6/8) (5 R 6/10), dark pink (near 10 RP 6/6), light purplish pink (near 10 RP 8/6), moderate purplish pink (7.5 RP 7/8), dark purplish pink (7.5 RP 6/8) (7.5 RP 6/6) (5 RP 6/8) (5 RP 6/6), moderate red (5 R 5/10) (5 R 5/8), moderate reddish orange (near 7.5 6/10) (7.5 R 6/8) (7.5 R 5/10) (7.5 R 5/8) and/or dark yellowish pink (near 7.5 R 6/6) in marginal areas and merging with translucent white basal areas. [7] Orientation at full bloom: Acute to recurve.

D. *Tube forming series.*—[1] General: Tepals basally united to form hollow perianth tube that is inserted on ovary and equipped with irregular carina (keel) at throat. [2] Shape: (a) Perianth tube — Elongated and ellipsoidal in cross section. (b) Blades — Nearly zygomorphic and lanceolate with acute tips. Entire margins with sparse, irregular teeth mainly in apex areas. (c) Carina (keel) — Transcending and irregular. [3] Texture: (a) Perianth tube — Thick, succulent and slightly ribbed. (b) Blades — Translucent and silken. (c) Carina (keel) — Fleshy. [4] Blade Number: Usually 8 or 9. [5] Size (at full bloom): (a) Perianth tube — (1) Base to keel length: Usually between 24 and 30 mm. along axis of tube with average length differences between measurements along dorsal and ventral sides for respective specimens usually being between 2 and 6 mm. (2) Internal Major Axis (at throat): Usually between 6 and 11 mm. when measured perpendicular to axis at perianth tube. (3) Internal Minor Axis (at throat): Usually between 4 and 8 mm. when measured perpendicular to axis of perianth tube. (b) Blades — (1) Length (keel to tip): Usually between 22 and 36 mm. (2) Width (maximum): Usually between 8 and 16 mm. [6] Color (at full bloom): (a) Perianth tube — Translucent white with overtones of color usually dominated by purplish pink and/or pink hues commonly purplish white (5 RP 9/1), pale purplish pink (10 P 8/4) (2.5 RP 8/4) (5 RP 9/2) (5 RP 8/4) (5 RP 8/2) (7.5 RP 8/4), light purplish pink (5 RP 8/6), light pink (near 10 RP 8/4) and/or moderate pink (near 10 RP 8/4) in overtone. (b) Blades — Marginal blade area with color dominated by pink, purplish pink, yellowish pink, red and/or reddish orange hues and merging with translucent white basal areas. Commonly dark pink (10 RP 6/6) (near 5 R 6/6), deep pink (near 10 RP 6/10) (10 RP 6/8) (5 R 6/10) (5 R 6/8) (2.5 R 6/10) (2.5 R 6/8), strong pink (10 RP 7/8) (2.5 R 7/8), dark purplish pink (near 7.5 RP 6/8), strong yellowish pink (near 5 R 7/8), moderate red (near 5 R 5/10) (5 R 5/8), and/or moderate reddish orange (near 10 R 6/8) (7.5 R 6/10) (7.5 R 6/8) (near 7.5 R 5/10) (7.5 R 5/8). (c) Carina (keel) — Commonly strong reddish purple (near 10 P 4/10) (2.5 RP 4/10) and/or deep reddish purple (near 10 P 3/10) (near 10 P 3/8) (2.5 RP 3/10) (near 2.5 RP 3/8). [7] Orientation (at full bloom): Erect to recurve.

E. *Androecium (stamens).*—[1] General: Numerous exserted and diadelphous stamens with one group having filaments basally fused to the perianth tube and the other group having filaments basally united to form a nectary housing, thin annulus around the style which is provided with a thin, deflexed, irregularly toothed margin or ruffle at the throat of the annulus. [2] Stamen Number: (a) Tube attached group — Usually between 89 and 95. (b) Basally united group — Usually between 17 and 23. [3] Filaments: (a) General — Translucent and glabrous with anther connective. (b) Shape — Long, slender and terete. (c) Texture — Glabrous and silken. (d) Color — Translucent white. (e) Size (at full bloom) — (1) Length: (a) Tube attached group — Usually between 32 and 47 mm. (b) Basally united group — Usually between 36 and 47 mm. (2) Diameter: Usually between 0.2 mm. and 0.3 mm. intermediate the opposite ends. [4] Anthers: (a) General — Adnate with four longitudinally dehiscent pollen sacs. (b) Shape — Elongated. (c) Texture — Waxy. (d) Color (post dehiscence) — Commonly light greenish yellow (10 Y 9/6) (near 7.5 Y 9/8) (near 7.5 Y 9/6), brilliant greenish yellow (near 7.5 Y 9/8) and/or light yellow (5 Y 9/6).

F. *Gynoecium (pistil).*—[1] General: Compound, pariental placentation with united style surrounded by annular diffuse nectary at its insertion. [2] Style: (a) General — Stout and inserted in ovary. (b) Shape — Elongated and terete. (c) Texture — Fleshy and glabrous with short inner glutinous hairs at distal end. (d) Color — Commonly strong reddish purple (2.5 RP 5/10), moderate reddish purple (10 RP 4/10), deep purplish pink (5 RP 6/10) and/or moderate purplish red (5 RP 5/8) (near 7.5 RP 4/8). (e) Size (at full floom) — (1) Length: Usually between 51 and 55 mm. (2) Diameter: Usually between 0.8 and 1.0 mm. intermediate the opposite ends. [3] Stigma: (a) General — Exserted and erect with usually 6 or 7 inner marginally adhering lobes. (b) Shape — Elongated and tapered toward lobe tips and having relatively blunt apices. (c) Texture — Fleshy and smooth with short glutinous hairs. (d) Color — Commonly strong reddish purple (10 P 5/10) (2.5 RP 5/10) (near 2.5 RP 4/10) and/or moderate reddish purple (near 10 P 5/8) (2.5 RP 5/8) (near 2.5 RP 5/6). (e) Size (lobe length at full bloom) — Usually between 3.5 and 5.2 mm. [4] Ovary: (a) General — Epigynous with thin epidermis and distally located concavity and with a single cavity having 6 or 7 carpels with numerous ovules. (b) Shape — Terete to ovid and generally broadening from insertion to floral end and externally ribbed. (c) Texture — Succulent and glabrous with thin outer epidermis. (d) Color — Commonly light yellow green (5 GY 8/6) (near 5 GY 8/4) (2.5 GY 8/6) (near 2.5 GY 8/4), moderate yellow green (near 5 GY 7/6) (5 GY 6/6) (5 GT 5/5) (2.5 GY 7/6) (2.5 GY 6/6) and/or strong yellow green (2.5 GY 6/8). (e) Size (at full bloom) — (1) Length (insertion to concavity base): Usually between 9 and 11 mm. (2) Major Axis (distal end of concavity): Usually between 7 and 10 mm. (3) Minor Axis (distal end of concavity): Usually between 6 and 9 mm.

Growing characteristics: A fast growth rate that is comparable to that of the 'Kris Kringle' variety with an upright and compact appearance as evidenced by erect stems with heavy (frequent) branching with or without pruning, and a natural tendency to branch without inducement by pruning during the growth period prior to blooming and which is comparable to that of the 'Kris Kringle' variety. Good resistances to nutrient deficiencies and fungus type diseases and which are comparable to those of the 'Kris Kringle' and 'Lavender Doll' varieties and a substantially greater resistance to flower bud abscission in comparison to the 'Lavender Doll' and 'Kris Kringle' varieties. Generally less recurve in the tube forming tepals as compared to specimens of the 'Kris Kringle' variety and with a bloom life (from initial tepal separation to initial tepal withering) from about 6 to about 9 days.

The following is a general description of a specimen of the new plant variety that was grown from the propagation of a single phylloclade in a nursery at Winter Garden, Fla.

Age of Plant: 6 months from initial propagation.
Branches from propagated cuttings: 4.
Total number of phylloclades grown from cutting: 23.
General:

| Branch No. | No. of Phylloclades | Max. Length | No. of Tips |
|---|---|---|---|
| 1 | 6 | 142 mm. | 3 |
| 2 | 6 | 126 mm. | 3 |
| 3 | 5 | 148 mm. | 2 |
| 4 | 6 | 127 mm. | 3 |

Midribs:

| Branch No. | Length (avg.) | Thickness (avg.) |
|---|---|---|
| 1 | 47 mm. | 3.6 mm. |
| 2 | 42 mm. | 3.2 mm. |
| 3 | 40 mm. | 3.6 mm |
| 4 | 41 mm. | 3.0 mm. |

Wings:

| Branch No. | Center Thickness (avg.) | Max. Width (avg.) |
|---|---|---|
| 1 | 1.6 mm. | 14 mm. |
| 2 | 1.7 mm. | 12 mm. |
| 3 | 1.8 mm. | 14 mm. |
| 4 | 1.6 mm. | 12 mm. |

Teeth:

| Branch No. | No./Phylloclades (avg.) | Center Thickness | Areole to Apex Dimension (avg.) |
|---|---|---|---|
| 1 | 7 | 1.23 mm. | 4.1 mm. |
| 2 | 6 | 1.0 mm. | 3.3 mm. |
| 3 | 7 | 1.1 mm. | 4.8 mm. |
| 4 | 6 | .85 mm. | 3.9 mm. |

Phylloclade color: Moderate yellow green (5 GY 6/6) (5 GY 6/4) (7.5 GY 5/4).

The following is a general description of a flower of the new plant variety which bloomed in December on a plant grown under shaded glasshouse nursery conditions in Winter Garden, Fla.

Bloom life: 8 days.
Sepaloid series of tepals:
(1) *Number.*—10.
(2) *Size (at full bloom).*—(a) Maximum base-tip dimension: 21 mm. (b) Minimum base-tip dimension: 3 mm. (c) Maximum width dimension: 12 mm.
(3) *Color.*—Moderate yellow green (2.5 GY 7/6) (2.5 GY 7/4) in field of outer members. Moderate red (5 R 5/10) and moderate reddish orange (7.5 R 6/10) (7.5 R 6/8) in marginal blade areas and merging with translucent white basal areas.

Tube laminating series:
(1) *Number.*—5.
(2) *Size (at full bloom).*—(a) Maximum base-tip dimension: 42 mm. (b) Minimum base-tip dimension: 26 mm. (c) Maximum width dimension: 14 mm. (d) Minimum width dimension: 13 mm.
(3) *Color.*—Moderate red (5 R 5/10) in marginal area and merging with a translucent white basal area.

Tube forming series of tepals:
(1) *Number.*—9.
(2) *Size (at full bloom).*—(a) Perianth tube: (1) Base to keel length — 25 mm. (2) Interior major axis (at throat) — 8 mm. (3) Interior minor axis (at throat) — 6 mm. (b) Blades: (1) Maximum length (keel to tip) — 26.5 mm. (2) Minimum length (keel to tip) — 24 mm. (3) Maximum width — 13 mm. (4) Minimum width — 9 mm.
(3) *Color.*—(a) Perianth tube: Translucent white with overtone of pale purplish pink (10 P 8/4) (2.5 RP 8/4). (b) Blades: Moderate reddish orange (7.5 R 6/10) in marginal areas and merging with translucent white basal area. (c) Carina (keel): Deep reddish purple (2.5 RP 3/10).

Androecium:

(1) *Stamen number.*—(a) Tube attached group: 94 (b) Basally united group: 22.

(2) *Filaments.*—(a) Color: Translucent white. (b) Size (at full bloom): (1) Length — (a) Tube attached group: 38.5 mm. (avg.). (b) Basally united group: 41 mm. (avg.). (2) Diameter — 0.25 mm. intermediate the opposite ends.

(3) *Anthers.*—(a) Color (post dehiscence): Light greenish yellow (10 Y 9/6) (near 7.5 Y 9/8).

Gynoecium (pistil):

(1) *Style.*—(a) Color: Moderate reddish purple (10 RP 4/10). (b) Size (at full bloom): (1) Length — 52 mm. (2) Diameter — 0.9 mm. intermediate the opposite ends.

(2) *Stigma.*—(a) Color: Strong reddish purple (2.5 RP 5/10) (10 P 5/10). (b) Size: Lobe length about 4 mm.

(3) *Ovary.*—(a) Color: Moderate yellow green (5 GY 6/6) (5 GY 5/6) (2.5 GY 6/6). (b) Size (at full bloom) — (1) Length (insertion to concavity base) — 10 mm. (2) Major axis (distal end of concavity) — 9 mm. (3) Minor axis (distal end of concavity) — 8 mm.

We claim:

1. The new and distinct variety of the Cactaceae family substantially as herein shown and described and which has a growth habit providing specimens that combine the following principal distinguishing characteristics:

1. a fast growth rate as comparable to that of the 'Kris Kringle' variety,
2. a natural tendency to branch without inducement by pruning during the growth period prior to blooming and which is comparable to that of the 'Kris Kringle' variety,
3. resistances to nutrient deficiencies and fungus type diseases that are comparable to those of the 'Kris Kringle' and 'Lavender Doll' varieties,
4. a substantially greater resistance to flower bud abscission in comparison to the 'Lavender Doll' and 'Kris Kringle' varieties, and
5. a bloom with less recurve in the tube forming tepals in comparison to the 'Kris Kringle' variety and which commonly occurs from about 2 to 4 weeks earlier than bloom of the 'Peach Parfait' variety, and having
   a. a bloom life of from about 6 to about 9 days,
   b. a shorter style and perianth tube than those of the 'Kris Kringle' and 'Lavender Doll' varieties, and
   c. perianth tube laminating and forming tepals with marginal blade areas that in color are dominated by pink, purplish pink, yellowish pink, red and/or reddish orange hues.

* * * * *